United States Patent
Prücher et al.

(10) Patent No.: US 6,756,370 B1
(45) Date of Patent: Jun. 29, 2004

(54) PIPERIDINE ALCOHOLS

(75) Inventors: Helmut Prücher, Heppenheim (DE); Henning Böttcher, Darmstadt (DE); Karl-August Ackermann, Ober-Ramstadt (DE); Rudolf Gottschlich, Reinheim (DE); Christoph van Amsterdam, Darmstadt (DE); Christoph Seyfried, Seeheim-Jugenheim (DE); Jürgen Harting, Darmstadt (DE); Gerd Bartoszyk, Weiterstadt (DE); Hartmut Greiner, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/069,054

(22) PCT Filed: Aug. 8, 2000

(86) PCT No.: PCT/EP00/07664

§ 371 (c)(1),
(2), (4) Date: Feb. 21, 2002

(87) PCT Pub. No.: WO01/14332

PCT Pub. Date: Mar. 1, 2001

(30) Foreign Application Priority Data

Aug. 21, 1999 (DE) .......................................... 199 39 756

(51) Int. Cl.[7] .............................................. A61K 31/54
(52) U.S. Cl. ................ 514/225.5; 514/226.5; 514/228.8; 514/255.03; 514/257.03; 514/307; 514/314; 514/317; 514/326; 544/8; 544/47; 544/58.1; 544/72; 544/795; 544/357; 549/141; 549/176; 549/148; 549/153; 549/192; 549/196; 549/180; 549/207; 549/213

(58) Field of Search ................................. 546/141, 148, 546/153, 176, 180, 192, 193, 194, 196, 197, 198, 199, 200, 202, 203, 204; 544/58.6, 72, 295, 47, 49, 55, 58.5, 67, 68, 73, 98, 179, 180, 182, 242, 336, 353, 354, 357.8; 514/317, 326, 252.03, 255.05, 314, 307, 318, 319, 320, 321, 322, 324, 331, 247, 252.1, 252.02, 256, 269, 309, 312, 222.5, 276.5, 228.8, 229.2, 230.5, 241, 242

(56) References Cited

FOREIGN PATENT DOCUMENTS

| WO | WO 91 18602 | 12/1991 | |
|---|---|---|---|
| WO | 97/22583 | * 6/1997 | .................. 546/192 |

* cited by examiner

Primary Examiner—D. Margaret Seaman
Assistant Examiner—Raymond Covington
(74) Attorney, Agent, or Firm—Millen, White, Zelano & Branigan, P.C.

(57) ABSTRACT

The invention relates to compounds of formula (I), wherein $R^1$, $R^2$ and A have the meanings given in claim 1, are potent 5-$HT_{2A}$ antagonists and are suitable for treating psychoses, schizophrenia, depression, neurological disorders, impaired memory, Parkinson's disease, amyotrophic lateral sclerosis, Alzheimer's disease, Huntington's disease, eating disorders such as bulimia and anorexia nervosa, Pre-Menstrual Syndrome and/or for positively influencing obsessive-compulsive disorders, (OCD).

(I)

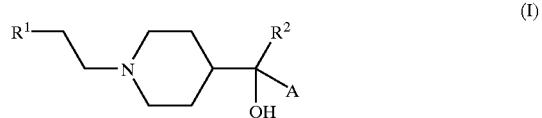

18 Claims, No Drawings

PIPERIDINE ALCOHOLS

The invention relates to compounds of the formula I

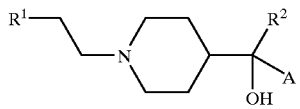

in which
$R^1$, $R^2$ in each case independently of one another are aryl or Het,
aryl is phenyl which is unsubstituted or mono-, di- or trisubstituted by Hal, CN, A, OA or OH,
Het is a mono- or binuclear unsaturated heterocyclic ring system which is unsubstituted or mono-, di- or trisubstituted by Hal, CN, A, OA or OH and which contains one, two or three identical or different heteroatoms such as nitrogen, oxygen and sulfur,
A is alkyl having 1–6 C atoms,
Hal is F, Cl, Br or I,
and their physiologically acceptable salts and solvates.

The invention was based on the object of finding novel compounds having valuable properties, in particular those which can be used for the production of medicaments.

It has been found that the compounds of the formula I and their physiologically acceptable salts and solvates have valuable pharmacological properties together with good tolerability, as they have actions on the central nervous system. The compounds have a strong affinity for 5-$HT_{2A}$ receptors; they furthermore exhibit 5-$HT_{2A}$ receptor-antagonistic properties.

Other compounds which also show 5-$HT_{2A}$-antagonistic actions are described, for example, in EP 0320983 or in WO 99/11641. 1-Phenylethyl-4-piperidinemethanol derivatives are described in EP 0208235 and in EP 0531410.

For the in-vitro detection of the affinity for 5-$HT_{2A}$ receptors, it is possible to use, for example, the following test (Example A1). The 5-$HT_{2A}$ receptors are exposed to both [$^3$H]ketanserin (a substance known for its affinity for the receptor) and the test compound. The decrease in the binding of [$^3$H]ketanserin to the receptor is a sign of the affinity of the test substance for the 5-$HT_{2A}$ receptor. Detection is carried out analogously to the description of J. E. Leysen et al., Molecular Pharmacology, 1982, 21: 301–314 or as also described, for example, in EP 0320983.

The experimental proof that the compounds according to the invention have affinity for the 5-$HT_{2A}$ receptor is demonstrated experimentally in vitro, as described above, for some representative compounds of the formula I. The pharmacological test data are summarized in Example A1, Table A. As a comparison, the compound (+)-α-(2,3-dimethoxyphenyl)-1-[2-(4-fluorophenyl)-ethyl]-4-piperidinemethanol, which is disclosed in EP 0531410, is additionally listed.

The efficacy of the compounds according to the invention as 5-$HT_{2A}$ receptor antagonists can be measured in vitro analogously to W. Feniuk et al., Mechanisms of 5-hydroxytryptamine-induced vasoconstriction, in: The Peripheral Actions of 5-Hydroxytryptamine, ed. Fozard JR, Oxford University Press, New York, 1989, p. 110. Thus the contractility of the rat tail artery, caused by 5-hydroxytryptamine, is mediated by 5-$HT_{2A}$ receptors. For the test system, vessel rings, prepared from the ventral rat tail artery, are subjected to perfusion with an oxygen-saturated solution in an organ bath. By introduction of increasing concentrations of 5-hydroxy-tryptamine into the solution, a response to the cumulative concentration of 5-HT is obtained. The test compound is then added to the organ bath in suitable concentrations and a second concentration curve is measured for 5-HT. The strength of the test compound on the shift of the 5-HT-induced concentration curve to higher 5-HT concentrations is a measure of the 5-$HT_{2A}$ receptor-antagonistic property in vitro.

The 5-$HT_{2A}$-antagonistic property can be determined in vivo analogously to M. D. Serdar et al., Psychopharmacology, 1996, 128: 198–205.

Serotonin-2(5-$HT_2$)agonists such as 1-(2,5-dimethoxy-4-iodophenyl)-2-aminopropane (DOI) induce sterotypic behaviour patterns such as, for example, head-twitching or ear-scratching in various animals such as, for example, mice or rats (N. A. Darmani et al., Pharmacol. Biochem. Behav. 1989, 36: 901–906; N. A. Darmani et al., Pharmacol. Biochem. Behav. 1990, 37: 95–99; N. A. Darmani et al., Pharmacol. Biochem. Behav. 1994, 48: 383–396; D. L. Willins and H. Y. Meltzer, J. Pharmacol. Exp. Ther., 1997, 282: 699–706). The response of head-twitching is selectively prevented by 5-$HT_{2A}$ antagonists, however ear-scratching is sensitive to 5-$HT_{2C}$ antagonists (N. A. Darmani et al., Pharmacol. Biochem. Behav. 1990, 37: 95–99; N. A. Darmani and C. F. Gerdes, Pharmacol. Biochem. Behav. 1995, 50: 545–550; D. L. Willins and H. Y. Meltzer, J. Pharmacol. Exp. Ther., 1997, 282: 699–706).

DOI-induced head-twitching in mice is used in order to test compounds having 5-$HT_{2A}$ antagonistic properties. The test compound is orally administered to male mice. 30 minutes later, 3 mg/kg of DOI is [sic] are administered intraperitoneally. The animals are observed for 15 minutes and the number of head twitches is noted. Quantification of the in vivo antagonistic effect of the test compounds ensues by comparison with the number of head twitches from those investigations in which the animals were only DOI-treated.

Surprisingly, the compounds according to the invention have, in comparison to the prior art, an improved suppression of the behaviour elicited on oral administration. The pharmacological test data are summarized in Example A2 in Table B. As a comparison, the compound (+)-α-(2,3-dimethoxyphenyl)-1-[2-(4-fluorophenyl)ethyl]-4-piperidinemethanol, which is disclosed in EP 0531410, is additionally listed.

The test results indicate an unexpectedly improved bioavailability of the compounds according to the invention in comparison to the prior art.

The compounds of the formula I are therefore suitable both in veterinary and in human medicine for the treatment of functional disorders of the central nervous system and also of inflammation. They can be used for the prophylaxis and for the control of the sequelae of cerebral infarcts (cerebral apoplexy) such as stroke and cerebral ischaemias and for the treatment of extrapyramidal motor side effects of neuroleptics and also of Parkinson's disease, for the acute and symptomatic therapy of Alzheimer's disease and the treatment of amyotrophic lateral sclerosis. They are likewise suitable as therapeutics for the treatment of brain and spinal cord traumata. In particular, however, they are suitable as pharmaceutical active compounds for anxiolytics, antidepressants, antipsychotics, neuroleptics, antihypertensives and/or for positively affecting compulsive behaviour (obsessive-compulsive disorder, OCD), anxiety states, panic attacks, psychoses, schizophrenia, anorexia, delusional obsessions, agoraphobia, migraine, Alzheimer's disease, sleep disorders, tardive dyskinesias, learning disorders, age-dependent memory disorders, eating disorders such as bulimia, drug abuse and/or sexual functional disorders.

In addition, they are suitable for the treatment of endocrine disorders such as hyperprolactinaemia, furthermore in vasospasms, hypertension and gastro-intestinal disorders.

They are furthermore suitable for the treatment of cardiovascular disorders and also extrapyramidal symptoms as described in WO 99/11641 on page 2, lines 24–30.

The compounds according to the invention are further suitable for decreasing intraocular pressure and for the treatment of glaucoma. They are also suitable in animals for the prophylaxis and treatment of symptoms of intoxication on the administration of ergovaline. The compounds are furthermore suitable for the treatment of disorders of the cardiovascular system (WO 99/11641, page 3, lines 14–15).

The compounds according to the invention can also be employed together with other active compounds in the treatment of schizophrenia. Possible other active compounds are the compounds mentioned in WO 99/11641 on page 13, lines 20–26.

They can furthermore be employed as intermediates for the production of further pharmaceutical active compounds.

The invention relates to the piperidine alcohols of the formula I and to their physiologically acceptable acid addition salts. The invention also relates to the solvates, e.g. hydrates or alcoholates, of these compounds.

The invention accordingly relates to the compounds of the formula I and a process for the preparation of compounds of the formula I according to claim 1.

The process for the preparation of compounds of the formula I according to claim 1 is characterized in that
a) a compound of the formula II

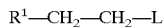  II in which L is Cl, Br, I or a free or reactively [sic] functionally modified OH group, and $R^1$ has the meaning indicated in claim 1, is reacted with a compound of the formula III

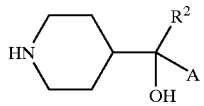  III in which $R^2$ and A have the meanings indicated in claim 1, or
b) a compound of the formula IV

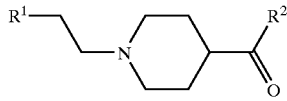  IV in which $R^1$ and $R^2$ have the meanings indicated in claim 1, is reacted with a compound of the formula V

  V in which R is iodine or bromine, X is Mg and A has the meaning indicated in claim 1, in a Grignard reaction, or
c) it is liberated from one of its functional derivatives by treating with a solvolysing or hydrogenolysing agent, or
d) a base of the formula I which is obtained is converted into one of its salts by treating with an acid.

The invention also relates to the compounds of the formula I according to claim 1, and to their physiologically acceptable salts and solvates as medicaments.

The invention relates in particular to the compounds of the formula I according to claim 1, and also their physiologically acceptable salts and solvates as medicaments having 5-$HT_{2A}$ receptor-antagonistic action.

The invention also relates to the compounds of the formula I, and their enantiomers and their salts.

For all radicals which occur a number of times, such as, for example, A or Hal, it holds true that their meanings are independent of one another.

The radical A is alkyl and has 1 to 6, preferably 1, 2, 3 or 4, in particular 1 or 2, C atoms. Alkyl is therefore in particular, for example, methyl, furthermore ethyl, n-propyl, isopropyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. A furthermore denotes completely or partially fluorinated or chlorinated alkyl radicals, such as, for example, trifluoromethyl or pentafluoroethyl. A is very particularly preferably methyl, ethyl, propyl, isopropyl or butyl.

OA is preferably methoxy, furthermore also ethoxy, n-propoxy, isopropoxy, n-butoxy, isobutoxy, sec-butoxy or tert-butoxy.

Hal is fluorine, chlorine, bromine or iodine, in particular fluorine or chlorine.

Aryl is unsubstituted, preferably—as indicated—monosubstituted phenyl, specifically preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-hydroxyphenyl, o-, m- or p-trifluoro-methoxyphenyl, o-, m- or p-cyanophenyl, o-, m- or p-methoxyphenyl, o-, m- or p-ethoxyphenyl, o-, m- or p-hydroxyphenyl, o-, m- or p-fluorophenyl, o-, m- or p-bromophenyl, o-, m- or p-chlorophenyl, o-, m- or p-difluoromethoxyphenyl, o-, m- or p-fluoromethoxyphenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,5- or 3,4-dimethoxyphenyl, 2,3,4-, 2,3,5-, 2,3,6-, 2,4,6- or 3,4,5-trichlorophenyl, 2,4,6-tri-tert-butylphenyl, furthermore preferably 3,5-ditri-fluoromethylphenyl, 2,5-dimethylphenyl, 2-hydroxy-3,5-dichlorophenyl, 2-fluoro-5- or 4-fluoro-3-trifluoromethylphenyl, 4-chloro-2- or 4-chloro-3-trifluoromethyl-, 2-chloro-4- or 2-chloro-5-trifluoromethylphenyl, 4-bromo-2- or 4-bromo-3-trifluoromethylphenyl, p-iodophenyl, 2,5-dimethoxy-4-nitrophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl or 2,4,6-triisopropylphenyl.

Het is preferably 2- or 3-furyl, 2- or 3-thienyl, 1-, 2 [sic] or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl [sic], 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, benzo[1,3]dioxol-4- or -5-yl, benzo[1,4]dioxan-5- or -6-yl, 3-, 4-, 5-, 6- or 7-benzisoxazolyl, 2-, 4-, 5-, 6- or 7-benzothiazolyl, 2-4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

Het is very particularly preferably 2- or 3-furyl, 2-or 3-thienyl, 4- or 5-thiazolyl, 4-pyridyl which is mono- or disubstituted by Hal or A.

$R^1$ is particularly preferably, for example, 2,3-dimethoxyphenyl, 2-, 3- or 4-fluorophenyl, 2,4-dichlorophenyl, 2,3- 2,4-, 3,4- or 2,6-difluoro-phenyl, 2- or 4-trifluoromethylphenyl, 2-, 3- or 4-tolyl, 2-chloro-6-fluorophenyl, 2-fluoro-4-trifluoromethylphenyl, 3-fluoro-5-trifluoromethylphenyl 4-fluoro-6-trifluoromethylphenyl, 3-fluoro-4-trifluoromethylphenyl, 2-fluoro-6-trifluoromethylphenyl, 4-cyanophenyl, thiophen-2- or 3-yl [sic], 5-chlorothiophen-2-yl, 5-methylthiophen-2-yl, 2,5-dichlorothiophen-3-yl, 2-chloro-3-methylthiophen-5-yl, bromothiophen-5-yl, 2-chloro-5-methylthiophen-4-yl, 2-methoxythiophen-5-yl, 2- or 4-methylthiazol-4- or -5-yl, and pyridin-4-yl.

$R^2$ is very particularly preferably phenyl, 4-chlorophenyl, 4-fluorophenyl, 2,4-difluorophenyl, 4-trifluoromethylphenyl, thiophen-2-yl, 5-chlorothiophen-2-yl, 2,5-dichlorothiophen-3-yl or benzodioxan-5- or 6-yl [sic].

Accordingly, the invention relates in particular to those compounds of the formula I in which at least one of the radicals mentioned has one of the preferred meanings indicated above. Some preferred groups of compounds can be expressed by the following subformulae Ia to Ig, which correspond to the formula I and in which the radicals not designated in greater detail have the meaning indicated in the formula I, but in which

| | | |
|---|---|---|
| in Ia | $R^1$ | is Het; |
| in Ib | $R^1$ | is Het, |
| | $R^2$ | is aryl; |
| in Ic | $R^1$ | is is [sic] Het or aryl, |
| | $R^2$ | is is [sic] aryl, |
| | Het | is is [sic] a mono- or binuclear unsaturated heterocyclic ring system which is unsubstituted or mono- or disubstituted by Hal, OA or A and which contains one or two identical or different heteroatoms such as nitrogen, oxygen and sulfur; |
| in Id | $R^1$ | is Het or aryl, |
| | $R^2$ | is aryl, |
| | Het | is a mono- or binuclear unsaturated heterocyclic ring system which is unsubstituted or mono- or disubstituted by Hal, OA or A and which contains one or two identical or different heteroatoms such as nitrogen, oxygen and sulfur; |
| | aryl | is phenyl which is unsubstituted or mono-, di- or trisubstituted by Hal, A, CN, OA or OH; |
| in Ie | $R^1$ | is Het or aryl, |
| | $R^2$ | is Het or aryl, |
| | Het | is thienyl, thiazolyl, pyridyl or benzo[1,4]dioxanyl, which is unsubstituted or mono- or disubstituted by Hal, OA or A, |
| | aryl | is phenyl which is unsubstituted or mono-, di- or trisubstituted by Hal, A, CN, OA or OH; |
| in If | $R^1$ | is Het or aryl, |
| | $R^2$ | is aryl, |
| | Het | is thienyl, thiazolyl or benzo[1,4]-dioxanyl, which is unsubstituted or mono- or disubstituted by Hal, OA or A, |
| | aryl | is phenyl which is unsubstituted or mono-, di- or trisubstituted by Hal or $CF_3$; |
| in Ig | $R^1$ | is Het, |
| | $R^2$ | is aryl, |
| | Het | is thienyl, thiazolyl or benzo[1,4]-dioxanyl, which is unsubstituted or mono- or disubstituted by Hal, OA or A, |
| | aryl | is phenyl which is unsubstituted or mono-, di- or trisubstituted by Hal or $CF_3$. |

The compounds of the formula I and also the starting substances for their preparation are otherwise prepared by methods known per se, such as are described in the literature (e.g. in the standard works such as Houben-Weyl, Methoden der Organischen Chemie [Methods of Organic Chemistry], Georg Thieme Verlag, Stuttgart; Organic Reactions, John Wiley & Sons, Inc., New York), namely under reaction conditions such as are known and suitable for the reactions mentioned. Use can also be made in this case of variants which are known per se, but not mentioned here in greater detail.

If desired, the starting substances for the claimed process can also be formed in situ in such a way that they are not isolated from the reaction mixture, but immediately reacted further to give the compounds of the formula I. On the other hand, it is possible to carry out the reaction stepwise.

In the compounds of the formula II, the radical L is preferably Cl or Br; however, it can also be I, OH or otherwise preferably a reactively [sic] functionally modified OH group, in particular alkylsulfonyloxy having 1–6 (e.g. methanesulfonyloxy) or arylsulfonyloxy having 6–10 C atoms (e.g. benzenesulfonyloxy, p-toluenesulfonyloxy, 1- or 2-naphthalenesulfonyloxy) or otherwise trichloromethoxy, alkoxy, such as, for example, methoxy, ethoxy, propoxy or butoxy, further more also phenoxy.

The compounds of the formula I can preferably be obtained by reacting compounds of the formula II with compounds of the formula III.

As a rule, the starting substances of the formulae II and III are known; the unknown compounds of the formulae II and III can easily be prepared analogously to the known compounds.

The reaction of the compounds II and III proceeds according to methods such as are known from the literature for the alkylation or acylation of amines. However, it is also possible to react the compounds in the presence of an indifferent solvent. Suitable solvents are, for example, hydrocarbons, such as benzene, toluene, xylene; ketones such as acetone, butanone; alcohols such as methanol, ethanol, isopropanol, N-butanol [sic]; ethers such as tetrahydrofuran (TRF) or dioxane; amides such as dimethylformamide (DMF) or N-methylpyrrolidone; nitrites such as acetonitrile, and, if appropriate, also mixtures of these solvents with one another or mixtures with water. The addition of an acid-binding agent, for example of an alkali metal or alkaline earth metal hydroxide, carbonate or bicarbonate or of another salt of a weak acid of the alkali or alkaline earth metals, preferably of potassium, sodium or calcium, or the addition of an organic base such as triethylamine, dimethylaniline, pyridine or quinoline or of an excess of piperidine derivative of the formula II can be favourable. Depending on the conditions used, the reaction time is between a few minutes and 14 days; the reaction temperature is between approximately 0 and 150°, normally between 20 and 130°.

The compounds of the formula I can also be obtained by reacting compounds of the formula IV with compounds of the formula V.

As a rule, the starting substances of the formulae IV and V are known; the unknown compounds of the formulae IV and V can easily be prepared analogously to the known compounds.

The reaction of the compounds IV and V proceeds according to methods such as are known from the literature for the Grignard reaction.

The compounds of the formulae [sic] I can furthermore be obtained by liberating them from their functional derivatives by solvolysis, in particular hydrolysis, or by hydrogenolysis.

Preferred starting substances for the solvolysis or hydrogenolysis are those which, instead of one or more free hydoxyl groups, contain corresponding protected hydroxyl groups. These are preferably compounds which, instead of the H atom of a hydroxyl group, carry a hydroxyl protective group, e.g. those which correspond to the formula I, but instead of a hydroxyl group contain an R"O-phenyl group (in which R" is a hydroxyl protective group).

The expression "hydroxyl protective group" is generally known and relates to groups which are suitable for protecting a hydroxyl group from chemical reactions, but which are easily removable after the desired chemical reaction has been carried out at other positions in the molecule. Typical groups of this type are, in particular, unsubstituted or substituted acyl-, aryl-, aralkoxymethyl- or aralkyl groups. The expression "acyl group" is to be interpreted in the widest sense in connection with the present process. It includes acyl groups derived from aliphatic, araliphatic, aromatic or heterocyclic carboxylic acids or sulfonic acids, in particular alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxybenzyloxycarbonyl.

The nature and size of the hydroxyl protective groups is not critical, as they are removed again after the desired chemical reaction or reaction sequence; groups having 1–20, in particular 1–10, C atoms are preferred. Examples of hydroxyl protective groups are, inter alia, benzyl, p-nitrobenzoyl [sic], p-toluenesulfonyl, tert-butyl and acetyl, benzyl and tert-butyl being particularly preferred. The liberation of the compounds of the formula I from their functional derivatives is carried out—depending on the protective group used—e.g. using strong acids, expediently using TFA or perchloric acid, but also using other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible, but not always necessary. Suitable inert solvents are preferably organic solvents, for example carboxylic acids such as acetic acid, ethers such as tetrahydrofuran or dioxane, amides such as DMF, halogenated hydrocarbons such as dichloromethane, in addition also alcohols such as methanol, ethanol or isopropanol, and also water. In addition, mixtures of the abovementioned solvents are suitable. TFA is preferably used in an excess without addition of a further solvent, perchloric acid in the form of a mixture of acetic acid and 70% strength perchloric acid in the ratio 9:1. The reaction temperatures for the cleavage are expediently between approximately 0 and approximately 50°; the reaction is preferably carried out at between 15 and 30° (room temperature).

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents in this case are those indicated above, in particular, for example, alcohols such as methanol or ethanol or amides such as DMF. As a rule, the hydrogenolysis is carried out at temperatures between approximately 0 and 100°and pressures between approximately 1 and 200 bar, preferably at 20–30° and 1–10 bar. Hydrogenolysis of the CBZ group takes place, for example, readily on 5 to 10% Pd/C in methanol or, using ammonium formate (instead of hydrogen), on Pd/C in methanol/DMF at 20–30°.

As a rule, the respective components are known or can be prepared by known processes as already described.

A base of the formula I obtained can be converted into the associated acid addition salt using an acid. For this reaction, suitable acids are those which yield physiologically acceptable salts. Thus inorganic acids can be used, e.g. sulfuric acid, hydrohalic acids such as hydrochloric acid or hydrobromic acid, phosphoric acids such as orthophosphoric acid, nitric acid, sulfamic acid, furthermore organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid.

The free bases of the formula I can, if desired, be liberated from their salts by treatment with strong bases such as sodium or potassium hydroxide, or sodium or potassium carbonate, if no further acidic groups are present in the molecule. In those cases where the compounds of the formula I have acidic groups, such as, for example, phenolic OH, salt formation can likewise be achieved by treatment with bases. Suitable bases are alkali metal hydroxides, alkaline earth metal hydroxides or organic bases in the form of primary, secondary or tertiary amines.

On account of their molecular structure, compounds of the formula I according to the invention can be chiral and can accordingly occur in two enantiomeric forms. They can therefore be present in racemic or in optically active form.

As the pharmaceutical activity of the racemates or the stereoisomers of the compounds according to the invention can differ, it may be desirable to use the enantiomers. In these cases, the final product or else even the intermediates can be resolved into enantiomeric compounds by chemical or physical measures known to the person skilled in the art or even employed as such in the synthesis.

In the case of racemic amines, diastereomers are formed from the mixture by reaction with an optically active resolving agent. Suitable resolving agents are, for example, optically active acids, such as the R and S forms of tartaric acid, diacetyltartaric acid, dibenzoyltartaric acid, mandelic acid, malic acid, lactic acid, suitably N-protected amino acids (e.g. N-benzoylproline or N-benzenesulfonylproline) or the various optically active camphorsulfonic acids. Chromatographic separation of enantiomers with the aid of an optically active resolving agent (e.g. dinitrobenzoylphenylglycine, cellulose triacetate or other derivatives of carbohydrates or chirally derivatized methacrylate polymers attached to silica gel) is also advantageous. Suitable eluents for this are aqueous or alcoholic solvent mixtures such as, for example, hexane/isopropanol/acetonitrile, e.g. in the ratio 82:15:3.

Under particular conditions, however, it is also possible even during the synthesis to employ corresponding enantiomerically pure intermediates which have been prepared by one of the abovementioned processes. In this case, the chirality is retained in the course of the further synthesis. Salts with physiologically unacceptable acids, e.g. picrates, can be used for the isolation and/or purification of the compounds of the formula I.

The invention furthermore relates to the medicaments according to the invention having 5-$HT_{2A}$ receptor-antagonistic action for the treatment of psychoses, schizophrenia, depression, neurological disorders, memory disorders, Parkinson's disease, amyotrophic lateral sclerosis, Alzheimer's disease, Huntington's disease, eating disorders such as bulimia, anorexia nervosa, premenstrual syndrome and/or for positively affecting compulsive behaviour (obsessive-compulsive disorder, OCD).

The invention also relates to a pharmaceutical preparation comprising at least one medicament according to the invention and also, if appropriate, vehicles and/or excipients and, if appropriate, other active compounds. In this case, the medicaments can be brought into a suitable dose form together with at least one solid, liquid and/or semiliquid vehicle or excipient and, if appropriate, in combination with one or more further active compound(s).

The invention furthermore relates to the use of the compounds according to the invention and/or of their physiologically acceptable salts and solvates for the production of a medicament having 5-$HT_{2A}$ receptor-antagonistic action.

The invention also relates to the use of the compounds according to the invention and/or of their physiologically acceptable salts and solvates for the production of a medicament having 5-$HT_{2A}$ receptor-antagonistic action for the treatment of psychoses, schizophrenia, depression, neurological disorders, memory disorders, Parkinson's disease, amyotrophic lateral sclerosis, Alzheimer's disease, Huntington's disease, eating disorders such as bulimia, anorexia nervosa, premenstrual syndrome and/or for positively affecting compulsive behaviour (obsessive-compulsive disorder, OCD).

The pharmaceutical preparations can be employed as medicaments in human and veterinary medicine. Suitable vehicles are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colourants, flavourings and/or aromatic substances. They can, if desired, also contain one or more further active compounds, e.g. one or more vitamins.

In this case, the substances according to the invention are as a rule administered in analogy to known preparations, preferably in doses between approximately 0.1 and 500 mg, in particular between 5 and 300 mg, per dose unit. The daily dose is preferably between approximately 0.01 and 250 mg/kg, in particular between 0.02 and 100 mg/kg, of body weight.

The specific dose for each intended patient depends, however, on all sorts of factors, for example on the efficacy of the specific compound employed, on the age, body weight, general state of health, sex, on the diet, on the time and route of administration, on the excretion rate, pharmaceutical combination and severity of the particular disorder to which the therapy applies. Oral administration is preferred.

Above and below, all temperatures are indicated in ° C. In the examples below, "customary working up" means: if necessary, the solvent is removed, if necessary, water is added, if necessary, the mixture is adjusted, depending on the constitution of the final product, to a pH of between 2 and 10 and extracted with ethyl acetate or dichloromethane, the organic phase is separated off, dried over sodium sulfate, filtered and concentrated, and the residue is purified by chromatography on silica gel and/or by crystallization.

Example A1

Preparation of a suspension of 5-$HT_{2A}$ receptors: Frontal rat cortex is homogenized in ice-cold buffer. The homogenate is centrifuged for 10 minutes at 4° C. and 50,000×[sic]. The pellet is resuspended in 2.5 ml of ice-cold tris buffer, made up with 10 ml of additional buffer and centrifuged as described [lacuna]. The pellet is then resuspended in buffer and diluted to give a homogenate which contains 60 mg of material/ml. 0.1 ml of the suspension, 100 µl of a 5 nM solution of [$^3$H]ketanserin, 100 µl of a solution of the test compound (concentration in the range from $10^{-5}$ to $10^{-10}$ mol per litre) are added to the incubation tubes and made up to 1 ml with buffer. The tubes are incubated for 15 minutes at 37° C. After termination of the incubation by immersing the tubes in an ice bath, the cooled suspension is filtered through a glass filter in vacuo. The filters are washed 3× with 5 ml of cold buffer and then transferred to scintillation tubes. The filters are analysed by means of liquid scintillation spectrometry in 8 ml of Triton X scintillator fluid.

The test results of the 5-$HT_{2A}$ receptor binding test by some representative compounds of the formula I are compiled in Table A below. The $IC_{50}$ values are indicated for the binding tests.

TABLE A

IC$_{50}$ values
(concentrations in mol/l at which 50% of the radioactive ligands are displaced from the binding sites)
of representative compounds of the formula I.

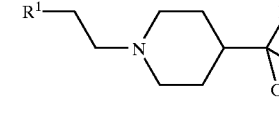

A = CH$_3$ (if not stated otherwise)

| R$^1$ | R$^2$ | Salt | Racemate (rac)/ enantiomer (+) or (−) | M.p. [° C.] | IC$_{50}$ |
|---|---|---|---|---|---|
| 5-chloro-thiophen-2-yl | 4-fluoro-phenyl | HCl | rac | 210–211 | 6.9E-10 |
| 5-chloro-thiophen-2-yl | 4-fluoro-phenyl | HCl | (+) | 210–211 | 1.1E-09 |
| thiophen-2-yl | 4-fluoro-phenyl | HCl | rac | 222–223 | 6.0E-09 |
| 4-fluoro-phenyl | 4-fluoro-phenyl | base | rac | 122–123 | 1.3E-09 |
| 4-fluoro-phenyl | 4-fluoro-phenyl | HCl | (−) | 185–186 | 5.7E-08 |
| 4-fluoro-phenyl | 4-fluoro-phenyl | HCl | (+) | 187–188 | 3.5E-10 |
| thiophen-3-yl | 4-fluoro-phenyl | base | rac | 94–95 | 2.2E-09 |
| thiophen-3-yl | 4-fluoro-phenyl | HCl | (−) | | 2.5E-07 |
| thiophen-3-yl | 4-fluoro-phenyl | HCl | (+) | | 3.3E-09 |
| 5-chloro-thiophen-2-yl* | 4-fluoro-phenyl | HCl | rac | 209–211 | 3.2E-08 |
| 2-methyl-thiazol-4-yl | 4-fluoro-phenyl | base | rac | 97–99 | 6.6E-08 |
| 5-chloro-thiophen-2-yl | 2,4-difluoro-phenyl | HCl | rac | 181–183 | 5.5E-09 |
| 4-fluoro-phenyl | 2,4-difluoro-phenyl | HCl | rac | 220–222 | 7.0E-10 |
| 4-fluoro-phenyl | 2,4-difluoro-phenyl | HCl | (−) | 212–214 | 2.2E-06 |
| 4-fluoro-phenyl | 2,4-difluoro-phenyl | HCl | (+) | 211–212 | 7.2E-10 |
| 5-methyl-thiophen-2-yl | 4-fluoro-phenyl | base | rac | 89 | 8.9E-10 |
| 2,4-dichloro-phenyl | 4-fluoro-phenyl | base | rac | 102–103 | 2.0E-09 |
| 4-pyridyl | 4-fluoro-phenyl | | rac | 77–78 | 2.2E-07 |
| 2,5-dichloro-thiophen-3-yl | 4-fluoro-phenyl | HCl | rac | 72.5 | 2.2E-09 |
| 2-chloro-3-methyl-thiophen-5-yl | 4-fluoro-phenyl | HCl | rac | 171–174 | 4.2E-09 |
| 5-bromo-thiophen-2-yl | 4-fluoro-phenyl | HCl | rac | 186–188 | 3.9E-09 |
| 2,4-difluoro-phenyl | 4-fluoro-phenyl | HCl | rac | 195–197 | 8.3E-10 |
| 2,4-difluoro-phenyl | 4-fluoro-phenyl | HCl | (−) | 202–204 | 4.0E-08 |
| 2,4-difluoro-phenyl | 4-fluoro-phenyl | HCl | (+) | 204–206 | 2.9E-09 |
| 2-chloro-5-methyl-thiophen-4-yl | 4-fluoro-phenyl | HCl | rac | 105 | 4.1E-09 |
| 5-methoxy-thiophen-2-yl | 4-fluoro-phenyl | HCl | rac | 174–175 | 2.1E-08 |
| 4-trifluoromethyl-phenyl | 4-fluoro-phenyl | HCl, hy-drate | rac | 69–72 | 3.2E-08 |
| 5-chloro-thiophen-2-yl | 4-trifluoromethyl-phenyl | HCl | rac | 196–198 | 8.6E-09 |
| 2-tolyl | 4-trifluoromethyl-phenyl | HCl | rac | 250–253 | 1.4E-09 |
| 4-cyano-phenyl | 4-fluoro-phenyl | HCl | rac | 227–228 | 2.7E-8 |
| 4-fluoro-phenyl | 2,3-di-methoxy-phenyl | HI | rac | 199–200 | 1.1E-08 |
| 5-chloro-thiophen-2-yl | phenyl | HI | rac | 177–178 | 8.3E-10 |
| 4-fluoro-phenyl | phenyl | HI | rac | 205–207 | 6.8E-10 |
| 4-fluoro-phenyl | 5-chloro-thiophen-2-yl | base | rac | 159–160 | 7.5E-10 |
| 5-chloro-thiophen-2-yl | 4-chloro-phenyl | HCl | rac | 192–193 | 2.6E-09 |
| 4-fluoro-phenyl | 4-chloro-phenyl | HCl | rac | 201–203 | 1.3E-09 |
| 4-fluoro-phenyl | benzo[1,4]-dioxan-5-yl | HCl | rac | 209–212 | 3.7E-09 |
| Comparison from EP 0531410 | | | | | |
| 4-fluoro-phenyl*** | 2,3-dimethoxy-phenyl | | | | 1-5E-10 |

*A = ethyl
***A = H

Example A2

TABLE B

Suppression of behaviour elicited (head-twitching in mice) by some representative compounds of the formula I (DOI antagonism)

A = CH$_3$ (if not stated otherwise)

| R$^1$ | R$^2$ | Salt | Racemate (rac)/ enantiomer (+) or (−) | M.p. [° C.] | Inhibition [%] |
|---|---|---|---|---|---|
| 5-chloro-thiophen-2-yl | 4-fluoro-phenyl | HCl | rac | 210–211 | |
| 5-chloro-thiophen-2-yl | 4-fluoro-phenyl | HCl | (+) | 210–211 | 21 |
| 5-chloro-thiophen-2-yl | 4-fluoro-phenyl | HCl | (−) | 210–211 | |

TABLE B-continued

Suppression of behaviour elicited (head-twitching in mice) by some representative compounds of the formula I (DOI antagonism)

$$R^1\text{-CH}_2\text{-CH}_2\text{-N}\diagdown\text{piperidine}\diagdown\text{C}(R^2)(A)(\text{OH})$$   I A = CH₃ (if not stated otherwise)

| R¹ | R² | Salt | Racemate (rac)/ enantiomer (+) or (−) | M.p. [° C.] | Inhibition [%] |
|---|---|---|---|---|---|
| 4-fluoro-phenyl | 2,4-difluoro-phenyl | HCl | (+) | 211–212 | |
| 2,4-difluoro-phenyl | 4-fluoro-phenyl | HCl | (+) | 204–206 | |
| 4-fluoro-phenyl | phenyl | HI | rac | 205–207 | |
| 4-fluoro-phenyl | 5-chloro-thiophen-2-yl | | rac | 159–160 | 26 |
| 5-chloro-thiophen-2-yl | 4-chloro-phenyl | HCl | rac | 192–193 | 28 |
| 4-fluoro-phenyl | 4-chloro-phenyl | HCl | rac | 201–203 | 96 |
| 4-fluoro-phenyl | benzo[1,4]-dioxan-5-yl | HCl | rac | 209–212 | 9 |
| 4-fluoro-phenyl | 4-trifluoro-methyl-phenyl | HCl | rac | 182–183 | 61 |
| Comparison from EP 0531410: | | | | | |
| 4-fluoro-phenyl*** | 2,3-di-methoxy-phenyl | | | | 0 |

***A = H

On oral administration, the compounds according to the invention exhibit improved suppression of the behaviour induced by DOI. This indicates an unexpected improvement in the bioavailability in comparison with the prior art.

Example B1

A solution of 0.88 g of 2-chloro-5-(2-chloro-ethyl)thiophene in 10 ml of acetonitrile is treated with 1.3 g of 1-(4-fluorophenyl)-1-piperidin-4-yl-ethanol, hydrochloride and 0.82 g of NaHCO₃ and stirred at 80° for 8 hours. After customary working-up, 1.3 g of 1-{1-[2-(5-chlorothiophen-2-yl)ethyl]piperidin-4-yl}-1-(4-fluorophenyl)ethanol are obtained. The residue is dissolved in acetone, treated with ether/HCl and the hydrochloride, m.p. 210–211°, is obtained after crystallization.

After separation of the racemate, the two enantiomers (+)-1-{1-[2-(5-chlorothiophen-2-yl)ethyl]piperidin-4-yl}-1-(4-fluorophenyl)ethanol, hydrochloride, specific rotation in methanol: +10.2° and (−)-1-{1-[2-(5-chlorothiophen-2-yl)ethyl]piperidin-4-yl}-1-(4-fluorophenyl)ethanol, hydrochloride, m.p. 210–211, specific rotation in methanol: −10.6°are obtained.

The compounds below are obtained analogously
1-{1-[2-(4-fluorophenyl)ethyl]piperidin-4-yl}-1-(4-fluorophenyl)ethanol, m.p. 122–123°, (+)-1-{1-[2-(4-fluorophenyl)ethyl]piperidin-4-yl}-1-(4-fluorophenyl)ethanol, hydrochloride, m.p. 187–188°, specific rotation in methanol: +10.3°; (−)-1-{1-[2-(4-fluorophenyl)ethyl]piperidin-4-yl}-1-(4-fluorophenyl)ethanol, hydrochloride, m.p. 185–186°, specific rotation in methanol: −10.6°; 1-{1-[2-(thiophen-2-yl)ethyl]piperidin-4-yl}-1-(4-fluorophenyl)ethanol, hydrochloride, m.p. 222–223°;

and also the compounds of the formula I listed in Table 1 below $$R^1\text{-CH}_2\text{-CH}_2\text{-N}\diagdown\text{piperidine}\diagdown\text{C}(R^2)(A)(\text{OH})$$   I A = CH (if not stated otherwise)

TABLE 1

| R¹ | R² | Salt | Racemate (rac)/enantiomer (+) or (−) | Rotation in methanol [°] | M.p. [° C.] |
|---|---|---|---|---|---|
| thiophen-3-yl | 4-fluoro-phenyl | | rac | | 94–95 |
| " | " | HCl | (−) | −12.0 | |
| " | " | HCl | (+) | +11.1 | |
| 5-chloro-thiophen-2-yl* | " | HCl | rac | | 209–211 |
| 5-chloro-thiophen-2-yl** | " | base | rac | | 122–124 |
| 2-methyl-thiazol-4-yl | " | base | rac | | 97–99 |
| 5-chloro-thiophen-2-yl | 2,4-di-fluoro-phenyl | HCl | rac | | 181–183 |
| 4-fluoro-phenyl | " | HCl | rac | | 220–222 |
| " | " | HCl | (−) | | 212–214 |
| " | " | HCl | (+) | | 211–212 |
| 5-methyl-thiophen-2-yl | 4-fluoro-phenyl | base | rac | | 89 |
| 4-methyl-thiazol-5-yl | " | oxalate, hydrate | rac | | 141–142 |
| 2,4-di-chloro-phenyl | " | base | rac | | 102–103 |
| 4-pyridyl | " | base | rac | | 77–78 |
| 2,5-di-chloro-thiophen-3-yl | " | HCl | rac | | 72.5 |
| 2-chloro-3-methyl-thiophen-5-yl | " | HCl | rac | | 171–174 |
| 5-bromo-thiophen-2-yl | " | HCl | rac | | 186–188 |
| 2,4-di-fluoro-phenyl | " | HCl | rac | | 195–197 |
| " | " | HCl | (−) | | 202–204 |
| " | " | HCl | (+) | | 204–206 |
| 2-chloro-5-methyl-thiophen-4-yl | " | HCl | rac | | 105 |
| 5-methoxy-thiophen-2-yl | " | HCl | rac | | 174–175 |

TABLE 1-continued

| R¹ | R² | Salt | Racemate (rac)/enantiomer (+) or (−) | Rotation in methanol [°] | M.p. [° C.] |
|---|---|---|---|---|---|
| 4-trifluoromethylphenyl | " | HCl, hydrate | rac | | 69–72 |
| 5-chlorothiophen-2-yl | 4-trifluoromethylphenyl | HCl | rac | | 196–198 |
| 4-fluorophenyl | " | HCl | rac | | 182–183 |
| 2-fluorophenyl | 4-fluorophenyl | HCl | rac | | 227–230 |
| 2-trifluoromethylphenyl | " | HCl | rac | | 207–210 |
| 2-tolyl | " | HCl | rac | | 250–253 |
| 2,6-difluorophenyl | " | HCl | rac | | 194–197 |
| 3,4-difluorophenyl | " | HCl | rac | | 204–206 |
| 2,3-difluorophenyl | " | HCl | rac | | 245–246 |
| 3-fluorophenyl | " | HCl | rac | | 240–241 |
| 2-chloro-6-fluorophenyl | " | HCl | rac | | 192–195 |
| 2-fluoro-4-trifluoromethylphenyl | " | HCl | rac | | 212–214 |
| 3-fluoro-5-trifluoromethylphenyl | " | HCl | rac | | 227–229 |
| 4-fluoro-2-trifluoromethylphenyl | " | HCl | rac | | 180 |
| 3-fluoro-4-trifluoromethylphenyl | " | HCl | rac | | 181–183 |
| 2-fluoro-6-trifluoromethylphenyl | " | HCl | rac | | 199–201 |
| 2-fluorophenyl | 2,4-difluorophenyl | HCl | rac | | 235–237 |
| 4-cyanophenyl | 4-fluorophenyl | HCl | rac | | 227–228 |

*A = ethyl
**A = isopropyl

Example B2

100 mg of Mg are introduced into 5 ml of abs. diethyl ether in an apparatus flushed with nitrogen and a solution of 0.25 ml of methyl iodide in 5 ml of abs. ether is added dropwise with stirring. After 20 minutes, a solution of 0.75 g of {1-[2-(2,3-di-methoxyphenyl)ethyl]piperidin-4-yl}-(4-fluorophenyl)-methanone in 10 ml of THF is added dropwise. The mixture is subsequently stirred for one hour and after customary working-up 0.36 g of 1-{1-[2-(2,3-dimethoxy-phenyl)ethyl]piperidin-4-yl}-1-(4-fluorophenyl)ethanol, hydroiodide, m.p. 199–200°, is obtained.

The compounds below are obtained analogously
1-{1-[2-(5-chlorothiophen-2-yl)ethyl]piperidin-4-yl}-1-phenylethanol, hydroiodide, m.p. 177–178°,
1-{1-[2-(4-fluorophenyl)ethyl]piperidin-4-yl}-1-phenylethanol, hydroiodide, m.p. 205–207°,
1-{1-[2-(4-fluorophenyl)ethyl]piperidin-4-yl}-1-(5-chlorothiophen-2-yl)ethanol, m.p. 159–160°,
1-{1-[2-(5-chlorothiophen-2-yl)ethyl]piperidin-4-yl}-1-(4-chlorophenyl)ethanol, hydrochloride, m.p. 192–193°,
1-{1-[2-(4-fluorophenyl)ethyl]piperidin-4-yl}-1-(4-chlorophenyl)ethanol, hydrochloride, m.p. 201–203°,
1-{1-[2-(4-fluorophenyl)ethyl]piperidin-4-yl}-1-(benzo[1,4]dioxan-5-yl)ethanol, hydrochloride, m.p. 209–212°.

The following examples relate to pharmaceutical preparations:

Example A

Injection Vials

A solution of 100 g of an active compound of the formula I and 5 g of disodium hydrogen phosphate in 3 l of double-distilled water is adjusted to pH 6.5 using 2 N hydrochloric acid, sterile-filtered, filled into injection vials, lyophilized and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of $NaH_2PO_4 \times 2H_2O$, 28.48 g of $NaH_2PO_4 \times 12H_2O$ and 0.1 g of benzalkonium chloride in 940 ml of double-distilled water. It is adjusted to pH 6.8, made up to 1 l and sterilized by irradiation. This solution can be used in the form of eye drops.

Example D

Ointment 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F

Coated Tablets

Analogously to Example E, tablets are pressed and are then coated in a customary manner with a coating of sucrose, potato starch, talc, tragacanth and colourant.

Example G

Capsules 2 kg of active compound of the formula I are filled into hard gelatin capsules in a customary manner such that each capsule contains 20 mg of the active compound.

Example H

Ampoules

A solution of 1 kg of active compound of the formula I in 60 l of double-distilled water is filled into ampoules, lyophilized under aseptic conditions and aseptically sealed. Each ampoule contains 10 mg of active compound.

What is claimed is:

1. A compound of formula I or a physiologically acceptable salt or solvate thereof

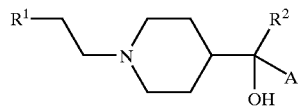

I in which $R^1$, $R^2$ in each case independently of one another are aryl or Het, aryl is phenyl which is unsubstituted or mono-, di-, or trisubstituted by Hal, CN, A, OA, or OH, Het is 2-furyl, 3-furyl, 2-theinyl, 3-theinyl, 1-pyrrolyl, 2-pyrrolyl, 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3-, or 4-4H-thiopyranyl[sic],3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, benzo[1,3]dioxol-4- or -5-yl, benzo[1,4]dioxan-5- or -6-yl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, A is alkyl having 1–6 C atoms, and Hal is F, Cl, Br, or I.

2. A process for the preparation of a compound of formula I, comprising reacting a compound of formula II

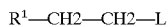

II in which L is Cl, Br, I or a free or relatively functionally modified OH group, and $R^1$ has the meaning indicated in claim 1, with a compound of formula III

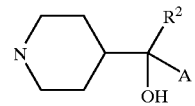

III in which R2 and A have the meanings indicated in claim 1, or b) reacting a compound of formula IV

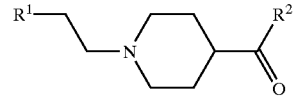

IV in which $R^1$ and $R^2$ have the meaning indicated in claim 1, with a compound of the formula V

V in which R is iodine or bromine, X is Mg and A has the meaning indicated in claim 1, in a Grignard reaction, or c) a compound of formula I is liberated from one of its functional derivative by treating said derivative with a solvolysing or hydrogenolysing agent, or d) a base of the formula I which is obtained is converted into one of its salts by treating with an acid.

3. A pharmaceutical composition comprising a compound of the formula I according to claim 1 and a pharmaceutically acceptable carrier.

4. A method for treating psychoses, schizophrenia, depression, a neurological disorder, a memory disorder, Parkinson's disease, amyotrophic lateral sclerosis, Alzheimer's disease, Huntington's disease, an eating disorder, premenstrual syndrome or a compulsive behaviour comprising administering to a host in need thereof a therapeutically effective amount of a compound according to claim 1.

5. A method for treating an indication which is mediated by a 5-HT$_{2A}$ receptor, comprising administering a therapeutically effective amount of a compound according to claim 1 to a host in need thereof.

6. The method according to claim 5 wherein the indication is psychoses, schizophrenia, depression, a neurological disorder, a memory disorder, Parkinson's disease, amyotrophic lateral sclerosis, Alzheimer's disease, Huntington's disease, bulimia, anorexia nervosa, premenstrual syndrome or obsessive compulsive disorder.

7. The compound according to claim 1, wherein said A is methyl, ethyl, n-propyl, isopropyl, n-butyl, sec-butyl, tert-butyl, pentyl, 1-methylbutyl, 2-methylbutyl, 3-methylbutyl, 1,1-dimethylpropyl, 1,2-dimethylpropyl, 2,2-dimethylpropyl, hexyl, 1-methylpentyl, 2-methylpentyl, 3-methylpentyl, 4-methylpentyl, 1,1 dimethylbutyl, 1,2-dimethylbutyl, 2,2-dimethylbutyl, 3,3-dimethylbutyl, 1-ethylbutyl, 2-ethylbutyl, 1-ethyl-1-methylpropyl, 1-ethyl-2-methylpropyl, 1,1,2-trimethylpropyl, or 1,2,2-trimethylpropyl.

8. The compound according to claim 1, wherein said OA is methoxy, ethoxy, n-propoxy, isopropoxy, n-butoxy, isobutosy, sec-butoxy, or tert-butoxy.

9. The compound according to claim 1, wherein said Aryl is phenyl, o-tolyl, m-tolyl, p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-hydroxyphenyl, o-, m- or p-trifluoromethoxyphenyl, o-, m- or p-cyanophenyl, o-, m- or p-methoxyphenyl, o-, m- or p-ethoxyphenyl, o-, m- or p-hydroxyphenyl, o-, m- or p-fluorophenyl, o-, m- or p-bromophenyl, o-, m- or p-chlorophenyl, o-, m- or p-difluoromethoxyphenyl, o-, m- or p-fluoromethoxyphenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-,2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,5- or 3,4-dimethoxyphenyl, 2,3,4-, 2,3,5-, 2,3,6-, 2,4,6- or 3,4,5-trichlorophenyl, 2,4,6-tri-tert-butylphenyl, furthermore preferably 3,5-ditrifluoro-methylphenyl, 2,5-dimethylphenyl, 2-hydroxy-3,5-dichlorophenyl, 2-fluoro-5- or 4-fluoro-3-tri-fluoromethylphenyl, 4-chloro-2- or 4-chloro-3-trifluoromethyl-, 2-chloro-4- or 2-chloro-5-trifluoromethylphenyl, 4-bromo-2- or 4-bromo-3-trifluoromethylphenyl, p-iodophenyl, 2,5-dimethoxy-4-nitrophenyl, 4-flouro-3-chlorophenyl, 4flouro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl or 2,4,6-triisopropylphenyl.

10. The compound according to claim 1, wherein said $R^1$ is 2,3-dimethoxyphenyl, 2-fluorophenyl, 3-fluorophenyl, 4-fluorophenyl, 2,4-dichlorophenyl, 2,3-2,4-, 3,4- or 2,6-difluorophenyl, 2- or 4-trifluoromethylphenyl, 2-, 3- or 4-tolyl, 2-chloro-6-fluorophenyl, 2-fluoro-4-trifluoromethylphenyl, 3-fluoro-5-trifluoromethylphenyl, 4-fluoro-6-trifluoromethylphenyl, 3-fluoro-4-trifluoromethylphenyl, 2-fluoro-6-trifluoromethylphenyl, 4-cyanophenyl, thiophen-2- or 3-yl [sic], 5-chlorothiophen-2-yl, 5-methylthiophen-2-yl, 2,5-dichlorothiophen-3-yl, 2-chloro-3-methylthiophen-5-yl, bromothiophen-5-yl, 2-chloro-5-methylthiophen-4-yl, 2-methoxythiophen-5-yl, 2- or 4-methylthiazol-4- or -5-yl, and pyridin-4-yl.

11. The compound according to claim 1, wherein said $R^2$ is phenyl, 4-chlorophenyl, 4-fluorophenyl, 2,4-difluorophenyl, 4-trifluromethylphenyl, thiopheny-2-yl, 5-chlorothiophen-2yl, 2,5-dichlorothiophen-3-yl, benzodioxan-5-yl, or benzodioxan-6-yl.

12. The compound according to claim 1, wherein said compound is 1-{1-[2-(5-chlorothiophen-2 yl)ethyl]piperidin-4-yl}-1-(4-fluorophenyl)ethanol.

13. A method for treating psychoses, schizophrenia, depression, a neurological disorder, a memory disorder, Parkinson's disease, amyotrophic lateral sclerosis, Alzheimer's disease, Huntington's disease, an eating disorder, premenstrual syndrome or a compulsive behaviour comprising administering to a host in need thereof a therapeutically effective amount of 1-{1-[2-(5-chlorothiophen-2 yl)ethyl]piperidin-4-yl}-1-(4-fluorophenyl)ethanol.

14. A method for treating an indication which is mediated by a 5-$HT_{2A}$ receptor comprising administering to a host in need thereof a therapeutically effective amount of 1-{1-[2-(5-chlorothiophen-2 yl)ethyl]piperidin-4-yl}-1-(4fluorophenyl)ethanol.

15. A method for treating a functional disorder of the central nervous system comprising administering a therapeutically effective amount of a compound according to claim 1.

16. A method for treating inflammation comprising administering a therapeutically effective amount of a compound according to claim 1.

17. A method for treating brain and spinal cord trauma comprising administering a therapeutically effective amount of a compound according to claim 1.

18. A compound of formula I or a physiologically acceptable salt or solvate thereof

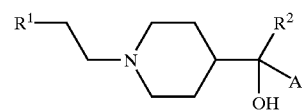

in which $R^1$ is 2,3-dimethoxyphenyl, 2-fluorophenyl, 3-fluorophenyl, 4-fluorophenyl, 2,4-dichlorophenyl, 2,3- 2,4-, 3,4- or 2,6-difluorophenyl, 2- or 4-trifluoromethylphenyl, 2-,3- or 4-tolyl, 2-chloro-6-fluorophenyl, 2-fluoro-4-trifluoromethylphenyl, 3-fluoro-5-trifluoromethylphenyl, 4-fluoro-6-trifluoromethylphenyl, 3-fluoro-4-trifluoromethylphenyl, 2-fluoro-6-trifluoromethylphenyl, 4-cyanophenyl, thiophen-2- or 3-yl [sic], 5-chlorothiophen-2-yl, 5-methylthiophen-2-yl, 2,5-dichlorothiophen-3-yl, 2-chloro-3-methylthiophen-5-yl, bromothiophen-5-yl, 2-chloro-5-methylthiophen-4-yl, 2-methoxythiophen-5-yl, 2- or 4-methylthiazol-4- or -5-yl, and pyridin-4-yl, $R^2$ is phenyl, 4-chlorophenyl, 4-fluorophenyl, 2,4-difluorophenyl, 4-trifluromethylphenyl, thiopheny-2-yl, 5-chlorothiophen-2yl, 2,5-dichlorothiophen-3-yl, benzodioxan-5-yl, or benzodioxan-6-yl, Hal, CN, A, OA, or OH, A is alkyl having 1–6 C atoms, and Hal is F, Cl, Br, or I.

* * * * *